(12) United States Patent
Beck (10) Patent No.: US 8,628,020 B2
(45) Date of Patent: Jan. 14, 2014

(54) FLEXIBLE WIRELESS PATCH FOR PHYSIOLOGICAL MONITORING AND METHODS OF MANUFACTURING THE SAME

(75) Inventor: James C. Beck, Berkeley, CA (US)

(73) Assignee: HMicro, Inc., Los Altos, CA (US)

( * ) Notice: Subject to any disclaimer, the term of this patent is extended or adjusted under 35 U.S.C. 154(b) by 85 days.

(21) Appl. No.: 12/739,561

(22) PCT Filed: Oct. 22, 2008

(86) PCT No.: PCT/US2008/080695
§ 371 (c)(1),
(2), (4) Date: Nov. 3, 2010

(87) PCT Pub. No.: WO2009/055415
PCT Pub. Date: Apr. 30, 2009

(65) Prior Publication Data
US 2011/0062241 A1    Mar. 17, 2011

Related U.S. Application Data

(60) Provisional application No. 60/982,402, filed on Oct. 24, 2007, provisional application No. 60/982,233, filed on Oct. 24, 2007.

(51) Int. Cl.
*G06K 19/06* (2006.01)
(52) U.S. Cl.
USPC ........................................... 235/492; 235/449
(58) Field of Classification Search
CPC .................................. G06K 19/0701–19/0709
USPC .................. 235/492, 493, 449, 486, 487, 380
See application file for complete search history.

(56) References Cited

U.S. PATENT DOCUMENTS

| 3,786,391 A | 1/1974 | Mathauser |
|---|---|---|
| 3,808,577 A | 4/1974 | Mathauser |
| 4,067,342 A | 1/1978 | Burton |

(Continued)

FOREIGN PATENT DOCUMENTS

| WO | WO 01/78594 A1 | 10/2001 |
|---|---|---|
| WO | WO 02/089667 A1 | 11/2002 |

(Continued)

OTHER PUBLICATIONS

International searc report and written opinion dated May 28, 2009 for PCT Application No. US08/80695.

(Continued)

*Primary Examiner* — Thien M Le
(74) *Attorney, Agent, or Firm* — Wilson Sonsini Goodrich & Rosati (57) ABSTRACT

Provided herein is an integrated wireless patch comprising a contact layer, an electronics layer, and a battery layer. The contact layer is a substrate having gel cutouts. The electronics layer can be folded into contact with the contact layer. The battery layer can be folded into contact with the electronic layer. Further provided herein is a method of manufacturing a wireless integrated patch comprising folding a substrate comprising at least one cutout, at least one contact disk in communication with a surface of a patient through the cutout, and battery terminals, wherein the at least one cutout, the at least on contact, and the battery terminals are adaptable to be located in different layers after the substrate is folded.

30 Claims, 4 Drawing Sheets

(56) References Cited

U.S. PATENT DOCUMENTS

| | | |
|---|---|---|
| 4,082,086 A | 4/1978 | Page et al. |
| 4,084,583 A | 4/1978 | Hjort |
| 4,121,573 A | 10/1978 | Crovella et al. |
| 4,365,634 A | 12/1982 | Bare et al. |
| 4,398,545 A | 8/1983 | Wilson |
| 4,653,503 A | 3/1987 | Heath |
| 5,372,125 A | 12/1994 | Lyons |
| 5,578,065 A | 11/1996 | Hattori et al. |
| 5,895,369 A | 4/1999 | Flower |
| 6,441,747 B1 | 8/2002 | Khair et al. |
| 6,456,720 B1 * | 9/2002 | Brimhall et al. ............... 381/324 |
| 6,897,788 B2 | 5/2005 | Khair et al. |
| 6,965,794 B2 | 11/2005 | Brody |
| 7,156,301 B1 * | 1/2007 | Bonalle et al. ................ 235/380 |
| 7,257,438 B2 | 8/2007 | Kinast |
| 7,668,580 B2 | 2/2010 | Shin et al. |
| 7,969,307 B2 | 6/2011 | Peeters |
| 7,970,450 B2 | 6/2011 | Kroecker et al. |
| 2003/0040305 A1 | 2/2003 | Ng et al. |
| 2006/0009691 A1 | 1/2006 | Yeo et al. |
| 2006/0155183 A1 | 7/2006 | Kroecker et al. |
| 2006/0264767 A1 | 11/2006 | Shennib |
| 2007/0060832 A1 | 3/2007 | Levin |
| 2007/0072443 A1 | 3/2007 | Rohrbach et al. |
| 2007/0093705 A1 | 4/2007 | Shin et al. |
| 2007/0179376 A1 | 8/2007 | Gerder |
| 2008/0309287 A1 * | 12/2008 | Reed ............................ 320/108 |
| 2009/0036792 A1 | 2/2009 | DeLuca et al. |
| 2010/0317958 A1 | 12/2010 | Beck et al. |
| 2010/0326703 A1 * | 12/2010 | Gilad et al. ................... 174/254 |
| 2011/0028822 A1 | 2/2011 | Beck et al. |
| 2011/0065476 A1 * | 3/2011 | Hsiao et al. ................... 455/558 |

FOREIGN PATENT DOCUMENTS

| | | |
|---|---|---|
| WO | WO 03/065926 A2 | 8/2003 |
| WO | WO 2003/065926 A3 | 6/2004 |
| WO | WO 2005/094674 A1 | 10/2005 |
| WO | WO 2006/061354 A1 | 6/2006 |
| WO | WO 2007/060609 A2 | 5/2007 |
| WO | WO 2007/060609 A3 | 10/2007 |
| WO | WO 2008/006150 A1 | 1/2008 |

OTHER PUBLICATIONS

International searc report and written opinion dated Jul. 20, 2009 for PCT Application No. US08/80659.
International searc report and written opinion dated Sep. 29, 2008 for PCT Application No. US08/64800.
Office action dated Apr. 15, 2013 for U.S. Appl. No. 12/601,373.
Office action dated Aug. 31, 2012 for U.S. Appl. No. 12/601,373.
Office action dated Nov. 21, 2012 for U.S. Appl. No. 12/739,553.
Office action dated Jul. 30, 2013 for U.S. Appl. No. 12/739,553.
Office action dated Oct. 29, 2013 for U.S. Appl. No. 12/601,373.

* cited by examiner

FLEXIBLE WIRELESS PATCH FOR PHYSIOLOGICAL MONITORING AND METHODS OF MANUFACTURING THE SAME

CROSS-REFERENCE

This application claims the benefit of U.S. Provisional Application Nos. 60/982,402, filed Oct. 24, 2007, and 60/982,233, filed Oct. 24, 2007, which applications are incorporated herein by reference in their entirety.

This application is related to U.S. Provisional Application No. 60/943,539, filed Jun. 12, 2007; and to PCT/US08/64800, filed on May 23, 2008 which claimed priority to U.S. Provisional Application No. 60/940,072, filed on May 24, 2007, which applications are incorporated herein by reference in their entirety.

BACKGROUND OF THE INVENTION

Monitoring physiological conditions of the human body is an important component of health care. Although the monitoring can be performed periodically by a health care professional, increasingly the task is being handled by electronics that connect the patient to a computerized system for data storage, presentation and retrieval. These electronic systems consist of sensors, signal conditioners, power sources and other components needed for the specific physiological conditions being monitored. Most sensors used in monitoring physically contact the body, requiring a method for connecting sensors to the rest of the electronic system. In the past, wires were the only option for this connection, but increasingly wireless methods are being employed. One such wireless design, [P1], describes a sensor patch that attaches to the patient during the monitoring period and sends physiological measurement data to the rest of the system over a radio link. This sensor patch includes interface electrodes, signal conditioning circuits, digitizing converters, a wireless data link (radio), support circuits and a power source (battery). Including all of these components in a patch that might be worn on the body for several days presents several design and manufacturing challenges. This patent describes a method for manufacturing such a patch.

SUMMARY OF THE INVENTION

Provided herein is an integrated wireless patch which comprises a contact layer comprising a substrate, an electronic layer folded into contact with the contact layer, and a battery layer folded into contact with the electronic layer. The battery layer comprises battery terminal tabs. Additionally, the battery layer can further comprise at least one antenna. The patch can be adaptable to be assembled by positioning the electronic layer between the contact layer and the battery layer. Furthermore, the patch can comprise an adhesive layer adaptable to be located between the contact layer and the electronic layer. In some embodiments, the patch can further comprise a battery. The contact layer can comprise at least one contact adaptable to be in communication with a surface of a patient. The contact layer can further comprise an adhesive surround positioned around the contact. Additionally, the patch can further comprise at least one antenna. The patch can also comprise at least one application-specific integrated circuit on the electronic layer.

Further provided herein is a method of manufacturing a wireless integrated patch comprising the steps of folding a substrate comprising at least one cutout, at least one contact disk in communication with a surface of a patient through the cutout, and battery terminals, wherein the at least one cutout, the at least on contact, and the battery terminals are adaptable to be located in different layers after the substrate is folded. Additionally, the method can comprise the step of attaching a battery to the battery terminals. Cutouts can be created in the substrate prior to the folding step. Furthermore, the method can further comprise the step fabricating at least one contact on the substrate prior to the folding step. In some embodiments of the method, the method can further comprise the step of attaching an ASIC to the substrate and further comprising the step of connecting the at least one contact to the ASIC with a trace. An antenna can be connected to the ASIC as part of the method. Additionally, an adhesive spacer can be inserted he between two layers of the folded substrate. The adhesive spacer can be inserted in between the cutout layer and the contact layer. The method can further comprise the step of applying gel to the cutout area on the contact layer. Furthermore, an adhesive washer can be attached to the cutout on the contact layer. In some embodiments, the method further comprises the step of cutting spiral cuts, the spiral cuts adaptable to surround the cutout. The method provided herein can further comprise more than one cutout on the contact layer and more than one contact on the electronics layer corresponding to the cutouts on the contact layer. Further provided herein is a wireless integrated patch produced according to the above described method.

Incorporation by Reference

All publications, patents, and patent applications mentioned in this specification are herein incorporated by reference to the same extent as if each individual publication, patent, or patent application was specifically and individually indicated to be incorporated by reference in their entirety.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Provided herein is an integrated wireless patch which comprises a contact layer comprising a substrate, an electronic layer folded into contact with the contact layer, and a battery layer folded into contact with the electronic layer. The battery layer comprises battery terminal tabs. Additionally, the battery layer can further comprise at least one antenna. The patch can be adaptable to be assembled by positioning the electronic layer between the contact layer and the battery layer. Furthermore, the patch can comprise an adhesive layer adaptable to be located between the contact layer and the electronic layer. In some embodiments, the patch can further comprise a battery. The contact layer can comprise at least one contact adaptable to be in communication with a surface of a patient. The contact layer can further comprise an adhesive surround positioned around the contact. Additionally, the patch can further comprise at least one antenna. The patch can also comprise at least one application specific integrated circuit (ASIC) on the electronic layer.

I. Devises

Figure 1:
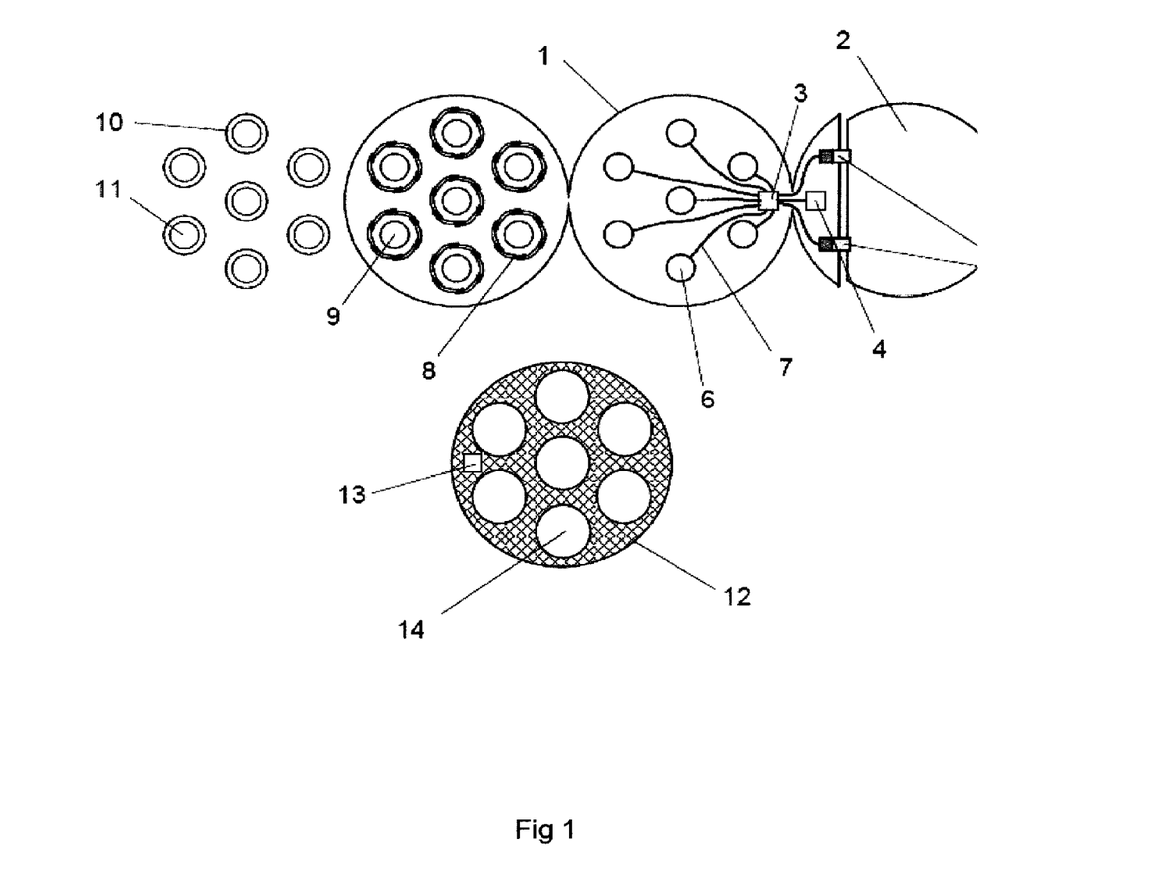
FIG. 1 illustrates an expanded view of one embodiment of an integrated patch.

FIG. 1 illustrates the components of a wireless patch. The wireless patch can use a multi-chip module or ASIC to integrate most of the needed functions into a single module. The ASIC can be a single chip device. In some embodiments, additional components can be added to the ASIC as needed. The FIG. 1 illustrates a substrate comprising a contact layer 1A, an electronics layer 1B, and a battery layer 1C. The contact layer 1A can come in contact with the surface of a patient. The contact layer can have gel cutouts 9. The gel cutouts 9 can be filled with a gel 11 that conducts an electrical signal from the surface of the patient. In some embodiments, the gel cutouts 9 can be surrounded by spiral cutouts 8. The spiral cutout 8 can provide flexibility between the contact layer and the skin of the patient and can serve to reduce strain between the contact layer and the skin surface. In some embodiments, the cutouts 9 of the contact layer 1A can have adhesive washers 10 that surround the cutouts 9. An electrode gel 11 can be used in conjunction with the adhesive washers 10 and the cutouts 9 to facilitate communication between the surface of the patient and the contacts 6 on the electronics layer 1B.

The electronics layer 1B comprises at least one contact pad 6. In some embodiments, multiple contact pads 6 can be fabricated on the electronics layer 1B, as shown in FIG. 1. The contact pads 6 can have conducting traces 7 that relay the signal sensed by the contact pads 6 to an application specific integrated circuit (ASIC) 3 located on the electronics layer 1B. The ASIC can be mounted directly on the substrate, with no additional support.

A battery can be used to power the patch. The battery can be in communication with the patch through the battery layer. In some embodiments, the battery layer 1C is a truncated circle, as shown in FIG. 1. In some embodiments, the battery layer can be substantially circular. The battery layer 1C, as shown in FIG. 1, can have battery terminals 5 that come in contact with a battery 2. The battery terminals can be spot welded or conductive glued to the battery layer. A cover or insulating film can be put over the top, with holes left for air access in the case of the battery is a zinc-air battery. The battery 2 powers the ASIC 3 through traces 7 between the battery terminals 5 and the ASIC 3. Additional support can be provided to the battery. The battery layer can further be adaptable to be used with a flat battery such as, for example purposes only, a watch battery, where the flat battery is mounted directly onto the battery layer.

In some embodiments, the battery layer 1C further comprises an antenna 4 that is in communication with the ASIC 3. Additionally, an input/output (I/O) used to communicate information from the patch to a user can be included on the battery layer. Input/outputs include, but are not limited to, light emitting diodes (LEDs), switches, or any other suitable indicator or actuator.

Additionally shown in FIG. 1 is an adhesive spacer 12. The adhesive spacer 12 can be located between the contact layer 1A and the electronics layer 1B, in order to prevent signal leakage between electrodes. The adhesive spacer can also be used to add a bit of thickness to keep the application specific integrated circuit projecting out too far from the electronics layer. A cutout 13 can be located on the adhesive spacer 12 to accommodate the ASIC 3 on the electronics layer 1B. Furthermore gel cutouts 14 of the adhesive spacer 12 can correspond to the gel cutouts 9 and contacts 6 of the contact layer 1A and the electronics layer 1B, respectively.

II. Methods of Manufacturing

Further provided herein is a method of manufacturing a wireless integrated patch comprising the steps of: folding a substrate comprising at least one cutout, at least one contact disk in communication with a surface of a patient through the cutout, and battery terminals, wherein the at least one cutout, the at least on contact, and the battery terminals are adaptable to be located in different layers after the substrate is folded. Additionally, the method can comprise the step of attaching a battery to the battery terminals. Cutouts can be created in the substrate prior to the folding step. Furthermore, the method can further comprise the step fabricating at least one contact on the substrate prior to the folding step. In some embodiments of the method, the method can further comprise the step of attaching an ASIC to the substrate and further comprising the step of connecting the at least one contact to the ASIC with a trace. An antenna can be connected to the ASIC as part of the method. Additionally, an adhesive spacer can be inserted he between two layers of the folded substrate. The adhesive spacer can be inserted in between the cutout layer and the contact layer. The method can further comprise the step of applying gel to the cutout area on the contact layer. Furthermore, an adhesive washer can be attached to the cutout on the contact layer. In some embodiments, the method further comprises the step of cutting spiral cuts, the spiral cuts adaptable to surround the cutout. The method provided herein can further comprise more than one cutout on the contact layer and more than one contact on the electronics layer corresponding to the cutouts on the contact layer. Further provided herein is a wireless integrated patch produced according to the above described method.

Provided herein is a method of manufacturing a wireless patch with integrated circuits and a battery. The patch can be manufactured using materials that are disposable or recyclable, while still meeting the technical requirements of the market for example purposes only, size, weight, battery life, functionality, comfort, among others. The process for manufacturing one embodiment of a wireless patch with integrated circuits is described below. While the steps of manufacturing such a wireless patch are outlined in one order, it should be noted that the steps for manufacturing the device can be done in any suitable order.

Figure 2A:
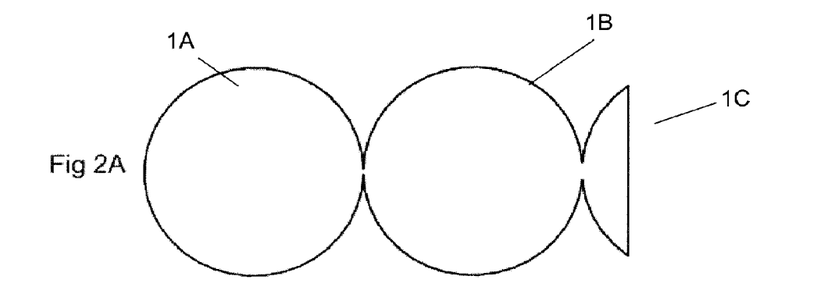
FIGS. 2A-2E illustrate one method for fabricating an integrated patch.

FIGS. 2A-2E illustrate one method for fabricating a wireless integrate patch. FIG. 2A illustrates a patch outline that has been cut from a piece of substrate material 1. In some embodiments, the substrate 1 is cut such that three separate sections are defined creating a first section 1A, a middle section 1B, and an end section 1C, as shown in FIG. 2A. The beginning section 1A corresponds to the contact layer, as described in FIG. 1. The middle section 1B and end section 1C correspond to the electronics layer and the battery layer, respectively. In some embodiments, the substrate is cut in one continuous strip. The substrate 1 can be cut so that the beginning section 1A and middle section 1B are cut in substantially the same shape, as seen in FIG. 2A. The end section 1C can be cut so that is only partially the size as the beginning and middle sections, as shown in FIG. 2A. Alternatively, the end section 1C can be cut so that the end section is the substantially the same shape as the beginning and middle sections.

Figure 2B:
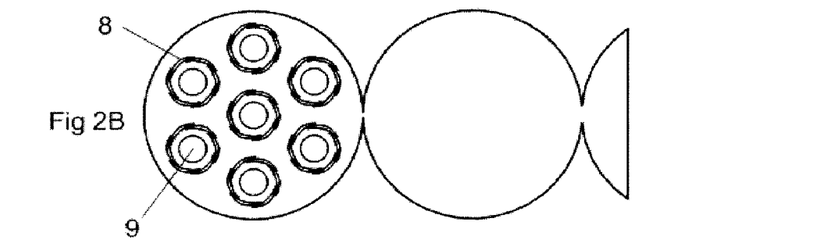

After the substrate has been cut to the desired shape and/or size, at least one cutout 9 can be formed in the beginning part 1A of the substrate 1. The cutout 9 can provide access between a contact disk 6 and the patient's skin. In some embodiments, multiple cutouts 9 are provided are shown in FIG. 2B. Additionally, spiral slots 8 can be cut in the substrate 1 surrounding the cutout 9. The spiral slot 8 can help to alleviate tension between the substrate and the surface of the skin, wherein the tension is caused by slight changes in the surface characteristics of the skin. The spiral slot surrounding the cutout has been previously described in U.S. Ser. No. 60/982,233 filed Oct. 24, 2007, entitled Multi-Electrode Sensing Patch for Long-term Physiological Monitoring with Swappable Electronics, Radio and Battery (Beck).

Figure 2C:
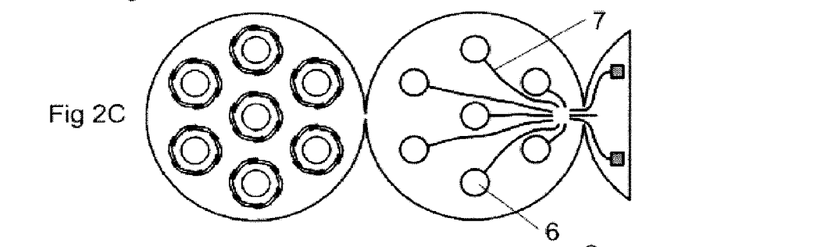

After the cutouts 9 have been formed, at least one contact disk 9 can be fabricated on the surface of the middle section 1B of the substrate. The contact can be fabricated from metal, polymer, or composite or any suitable combination thereof. The contact can be fabricated by any suitable method including, but not limited to, microfabrication, printing, chemical deposition or other techniques. Multiple contacts can be fabricated on the substrate, as shown in FIG. 2C. Any suitable number of contacts can be fabricated on the substrate. Traces 7 from the contacts 6 can also be fabricated. In addition to the contacts, battery contact points can be fabricated on the end section of the substrate.

Figure 2D:
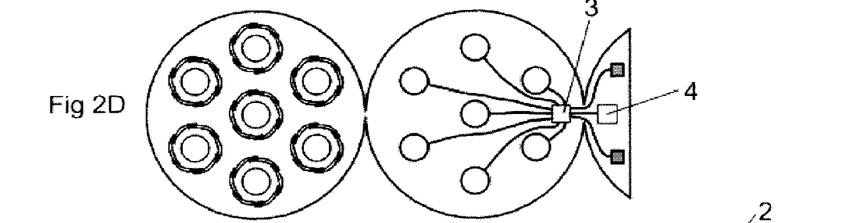
Figure 2E:
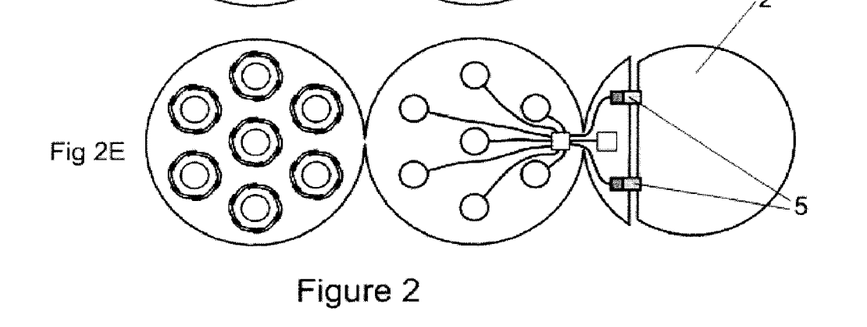

After the contacts and traces from the contact have been fabricated, an application specific integrated circuit 3 can be mounted on the substrate 1 as shown in FIG. 2D. Additionally, an antenna 4 can be mounted on the substrate 1. Before the device is folded into its final configuration a battery 2 can be attached to the substrate 1 at the battery terminals 5. The device can be folded after the battery has been attached. Alternatively, the device can be folded and then the battery attached.

Figure 3A:
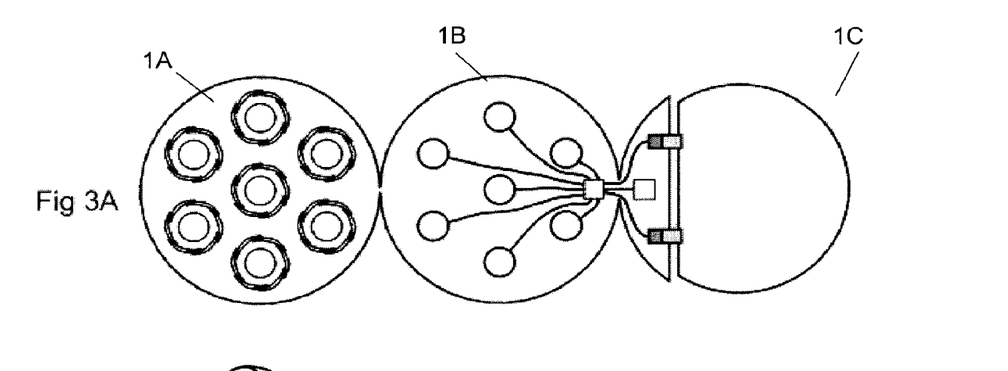
FIGS. 3A-3C illustrate one method for assembling an integrated patch.
Figure 3B:
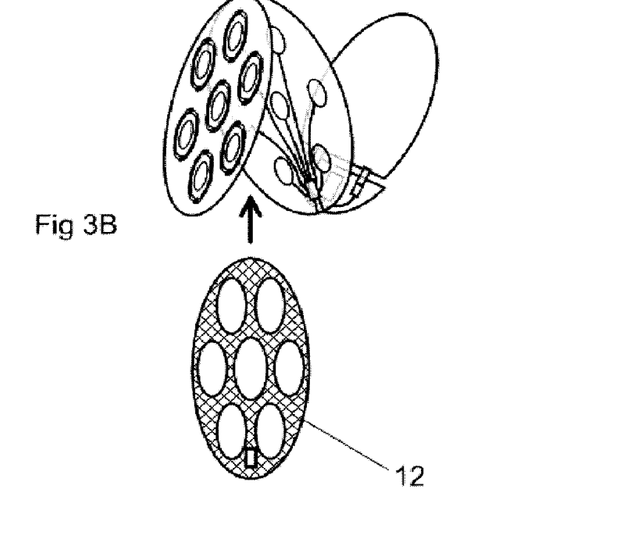
Figure 3C:
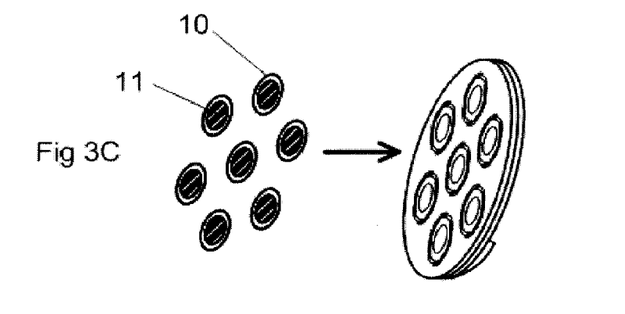

FIGS. 3A-3C illustrate a wireless integrated patch being assembled. FIG. 3A illustrates a fabricated wireless integrated patch before being assembled. The patch can then be assembled by folding the patch using a z-fold as shown in FIG. 3B, wherein the contact layer 1A is in contact with the electronics layer 1B, and the electronics layer 1B is in contact with the battery layer 1C. An adhesive spacer 12 can be inserted in between the contact layer 1B and the electronics layer 1C. Once the device is folded as shown in FIG. 3C, the adhesive washers 10 and gel 11 can be applied to the contact layer 1A.

Figure 4:
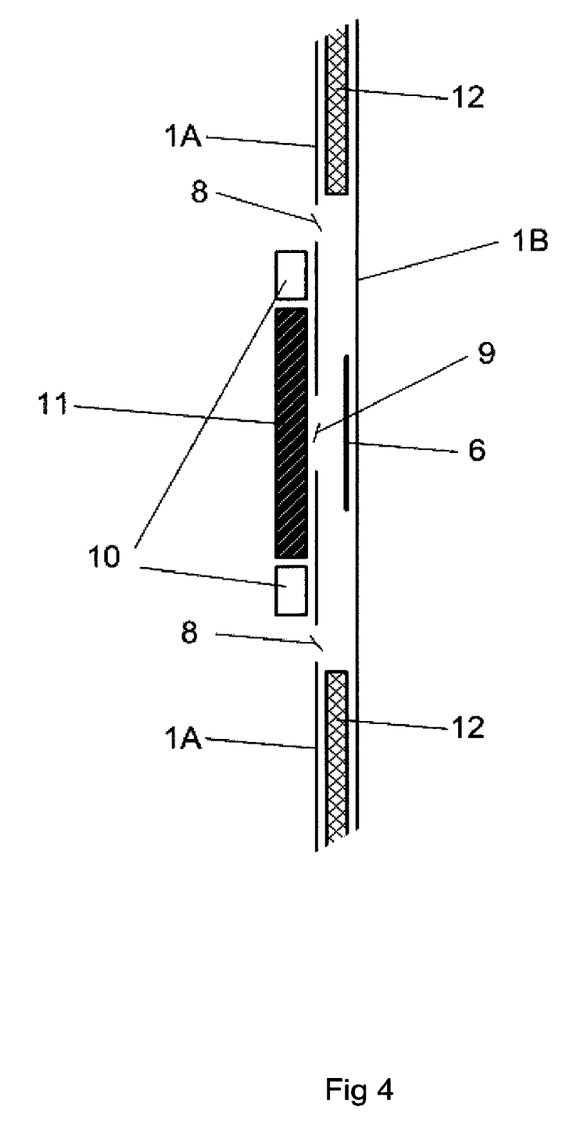
FIG. 4 illustrates a schematic cross-sectional view of one electrode of an integrated patch.

A schematic cross section of a portion of the patch is shown in FIG. 4, in particular the contact layer 1A and electronics layer 1B and related structures. As shown in FIG. 4, the contact layer 1A can be stacked on the electronics layer 1B with an adhesive spacer 12 located in between the contact layer 1A and the electronics layer 1B. The contact 6 on the electronics layer 1B is in communication with the surface of a patient through the gel cutout 9 on the contact layer 1A and electrode gel 11. In some embodiments, the contact layer 1A can be adhered to the skin of a patient using adhesive washers 10 surrounding the get cutout 9 of the contact layer 1A. Spiral cutouts 8 surrounding the gel cutout 9 can help alleviate any tension between the patch and the skin surface.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. An integrated wireless patch which comprises:
   a contact layer comprising a substrate;
   an electronic layer folded into contact with the contact layer;
   a battery layer folded into contact with the electronic layer; and
   an adhesive layer adaptable to be located between the contact layer and the electronic layer.

2. The patch of claim 1 wherein the battery layer comprises battery terminal tabs.

3. The patch of claim 1 wherein the battery layer further comprises at least one antenna.

4. The patch of claim 1 wherein the patch is adaptable to be assembled by positioning the electronic layer between the contact layer and the battery layer.

5. The patch of claim 1 further comprising a battery.

6. The patch of claim 1 wherein the contact layer comprises at least one contact adaptable to be in communication with a surface of a patient.

7. The patch of claim 6 wherein the contact layer further comprises an adhesive positioned around the contact.

8. The patch of claim 1 further comprising at least one antenna.

9. The patch of claim 1 further comprising at least one application-specific integrated circuit on the electronic layer.

10. A method of manufacturing a wireless integrated patch comprising:
    folding a substrate comprising at least one cutout, at least one contact disk in communication with a surface of a patient through the cutout, and battery terminals, wherein the at least one cutout, the at least on contact, and the battery terminals are adaptable to be located in different layers after the substrate is folded.

11. The method of claim 10 further comprising the step of attaching a battery to the battery terminals.

12. The method of claim 10 further comprising the step of creating a cutout in the substrate prior to the folding step.

13. The method of claim 10 further comprising the step fabricating at least one contact on the substrate prior to the folding step.

14. The method of claim 13 further comprising the step of attaching an ASIC to the substrate and further comprising the step of connecting the at least one contact to the ASIC with a trace.

15. The method of claim 14 further comprising the step of connecting an antenna to the ASIC.

16. The method of claim 10 further comprising the step of inserting an adhesive spacer between two layers of the folded substrate.

17. The method of claim 16 wherein the adhesive spacer is inserted in between the cutout layer and the contact layer.

18. The method of claim 10 further comprising the step of applying gel to the cutout area.

19. The method of claim 10 further comprising the step of attaching an adhesive washer around the cutout.

20. The method of claim 10 further comprising the step of cutting spiral cuts, the spiral cuts adaptable to surround the cutout.

21. A wireless integrated patch produced according to the method of claim 10.

22. The method of claim 10 further comprising more than one cutout and more than one contact.

23. An integrated wireless patch which comprises:
    a contact layer comprising a substrate;
    an electronic layer folded into contact with the contact layer; and a battery layer folded into contact with the electronic layer,
wherein the contact layer comprises at least one contact adaptable to be in communication with a surface of a patient.

24. The patch of claim 23 wherein the battery layer comprises battery terminal tabs.

25. The patch of claim 23 wherein the battery layer further comprises at least one antenna.

26. The patch of claim 23 wherein the patch is adaptable to be assembled by positioning the electronic layer between the contact layer and the battery layer.

27. The patch of claim 23 further comprising a battery.

28. The patch of claim 23 wherein the contact layer further comprises an adhesive positioned around the contact.

29. The patch of claim 23 further comprising at least one antenna.

30. The patch of claim 23 further comprising at least one application-specific integrated circuit on the electronic layer.

* * * * *

UNITED STATES PATENT AND TRADEMARK OFFICE
CERTIFICATE OF CORRECTION

PATENT NO. : 8,628,020 B2  Page 1 of 1
APPLICATION NO. : 12/739561
DATED : January 14, 2014
INVENTOR(S) : James C. Beck It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 400 days.

Signed and Sealed this
Twenty-second Day of September, 2015

Michelle K. Lee
*Director of the United States Patent and Trademark Office*